(12) United States Patent
Atmanspacher (10) Patent No.: US 11,098,421 B2
(45) Date of Patent: Aug. 24, 2021

(54) KNITTED FABRIC PANEL

(71) Applicant: medi GmbH & Co. KG, Bayreuth (DE)

(72) Inventor: Jan Atmanspacher, Warmensteinach (DE)

(73) Assignee: MEDI GMBH & CO. KG, Bayreuth (DE)

( * ) Notice: Subject to any disclaimer, the term of this patent is extended or adjusted under 35 U.S.C. 154(b) by 112 days.

(21) Appl. No.: 16/598,092

(22) Filed: Oct. 10, 2019

(65) Prior Publication Data

US 2020/0115830 A1     Apr. 16, 2020

(30) Foreign Application Priority Data

Oct. 16, 2018   (EP) ................................ 18200645

(51) Int. Cl.
| | | |
|---|---|---|
| *D04B 1/12* | (2006.01) | |
| *A61F 13/08* | (2006.01) | |
| *D04B 1/02* | (2006.01) | |
| *D04B 1/10* | (2006.01) | |
| *D04B 1/26* | (2006.01) | |

(52) U.S. Cl.
CPC .............. *D04B 1/126* (2013.01); *A61F 13/08* (2013.01); *D04B 1/02* (2013.01); *D04B 1/102* (2013.01); *D04B 1/265* (2013.01); *D10B 2403/02* (2013.01); *D10B 2501/043* (2013.01)

(58) Field of Classification Search
CPC .......... D04B 1/126; D04B 1/26; D04B 1/265; D04B 1/02; D04B 1/102; D10B 2509/28
See application file for complete search history.

(56) References Cited

U.S. PATENT DOCUMENTS

| | | | |
|---|---|---|---|
| 5,335,517 A  *  | 8/1994 | Throneburg ........... | A41B 11/00 2/239 |
| 7,441,419 B1 | 10/2008 | Dollyhite | |
| 9,506,172 B2 | 11/2016 | Atmanspacher | |
| 10,494,747 B2 * | 12/2019 | Atmanspacher ....... | D04B 1/265 |
| 2006/0144097 A1 | 7/2006 | Langer | |
| 2009/0275873 A1* | 11/2009 | Achtelstetter ........... | D04B 1/18 602/76 |

(Continued)

FOREIGN PATENT DOCUMENTS

| | | | |
|---|---|---|---|
| DE | 102013103914 B3 | | 3/2014 |
| EP | 0854219 A2 | | 7/1998 |

(Continued)

OTHER PUBLICATIONS

European Search Report, EP18200645, dated Jan. 29, 2019.

*Primary Examiner* — Danny Worrell
(74) *Attorney, Agent, or Firm* — Lucas & Mercanti, LLP; Klaus P. Stoffel (57) ABSTRACT

A knitted fabric panel, composed of a knitted base fabric embroidered as a circular knitted fabric from at least one knitted base fabric thread, wherein at least one zone having a reduced thread volume is provided, the zone being knitted by further threads which by way of the two ends thereof are fixed in the knitted base fabric, at least part of the further threads being thinner than the knitted base fabric thread. The threads instead of the knitted base fabric thread are knitted in a plurality of separate loop forming courses that in the circumferential direction extend by less than 360°.

20 Claims, 5 Drawing Sheets

(56) References Cited

U.S. PATENT DOCUMENTS

2012/0289875 A1* 11/2012 Matsuo .................. A41D 13/08
                                                        602/20
2014/0316312 A1* 10/2014 Atmanspacher ....... A61H 1/008
                                                        601/84

FOREIGN PATENT DOCUMENTS

EP         1668998 A1    6/2006
WO      2016097267 A1    6/2016

* cited by examiner

KNITTED FABRIC PANEL

CROSS-REFERENCE TO RELATED APPLICATIONS

The present application claims priority of EP 18 200 645.2, filed Oct. 16, 2018, the priority of this application is hereby claimed and this application is incorporated herein by reference.

BACKGROUND OF THE INVENTION

The invention relates to a knitted fabric panel, composed of a knitted base fabric knitted as a circular knitted fabric from at least one knitted base fabric thread.

Knitted fabric panels, for example in the form of a leg or arm stocking or of a bandage, etc., are often pulled over a joint. The knitted fabric material in the bend of the joint is often pushed together when the joint is bent and folds are formed. This formation of folds, for example in the region of the hollow of the knee or the crook of the arm is often perceived to be uncomfortable, in particular when a specific pressure by way of the knitted fabric panel is to be exerted on the underlying tissue, for example in the embodiment of the knitted fabric panel as a compression stocking.

In order to counteract this, it is known for a zone having a larger loop width, or larger loops, respectively, in the knitted base fabric be provided in the joint region or in the region of the bend of the joint, respectively, so as to therein reduce the thread volume and to implement a type of "comfort zone". This larger loop width, or enlargement of the loops per se, however is already disadvantageous in visual terms since a visually heavily distorted loop appearance or knitted fabric appearance results in this region, since the significantly larger loops are visible and are perceived as a type of perforation. On account of this modified loop appearance, any potential pressure gradient to be generated, when viewed in the circumferential and longitudinal direction of the knitted fabric panel, such as is provided in a defined manner in knitted compression fabric panels, for example, is also modified. This is because a decrease in pressure on account of the significant enlargement of the loops results in this region.

SUMMARY OF THE INVENTION

The invention is based on the object of specifying a knitted fabric panel that is improved in comparison to the above.

In order for said object to be achieved, it is provided according to the invention in the case of a knitted fabric panel of the type mentioned at the outset that at least one zone having a reduced thread volume is provided, said zone being knitted by means of further threads which by way of the two ends thereof are fixed in the knitted base fabric, at least part of said further threads being thinner than the knitted base fabric thread, wherein the threads instead of the knitted base fabric thread are knitted in a plurality of separate loop-forming courses that in the circumferential direction extend by less than 360°.

In the case of the knitted fabric panel according to the invention, a targeted defined reduction of the thread volume is performed in at least one zone so that less "thread mass" is present in this zone as compared to the neighboring knitted base fabric region. This takes place in that the knitted base fabric thread that is knitted in a quasi-helically encircling manner in this zone is locally and, when viewed in the circumferential direction, partially replaced by a further thread, wherein at least part of said replacement threads is thinner than the knitted base fabric thread. The knitted base fabric thread in terms of the helical encircling action thereof is thus locally interrupted, and instead a further thread which in turn is encircling by less than 360°, preferably by less than 270°, in particular by approx. 180° or less, is interknitted so as to achieve a local, quasi-"thinned out" zone.

The interrupted knitted base fabric thread, as well as the further thread, is in each case fixed, or "locked", consequently fixedly integrated, in the knitted base fabric or in the knitted fabric region that comprises the zone, respectively. In this way it is possible for the knitted base fabric thread and each of the further threads, when viewed in the circumferential direction, to be interknitted and integrated so as to be mutually contiguous, while said threads in the longitudinal direction of the knitted fabric, thus in the direction of the stitch wales, are interknitted in a loop-forming manner.

The size of the interknitted zone can be varied depending on how many further threads are interknitted in how many loop courses, and on how far the further threads are encircling. Since at least part of the interknitted further threads are thinner than the knitted base fabric thread, a reduction in the thread volume thus inevitably results in this zone, or in the region of said part-courses in which the further threads are only partially interknitted, respectively, this reduction leading to a reduced formation of folds in the joint region and consequently providing more wear comfort. Since the loop formation per se is not modified since the loop width or loop size, respectively, remains the same and only the thread thickness is varied, a consistent loop appearance or knitted fabric appearance results despite the integration of these partial zones such that this region, to the extent that said region is not consciously promoted, as will yet be discussed hereunder, in visual terms cannot be seen at a first glance but nevertheless has the described advantages, in particular in terms of the formation of folds. When this is a knitted fabric panel with a lower or greater compressive property, the pressure profile can also be maintained since firstly the weft thread, which is preferably an elastic weft thread, also runs through the loops knitted by way of the further threads, consequently also runs through the zone, and secondly the interknitted further threads have a corresponding elasticity, for example comparable to that of the knitted base fabric thread, such that no modification results in terms of a compressive force exerted in the region of the zone. The loop size by way of which the further individual threads are interknitted is thus identical to that of the remaining knitted fabric that is knitted across the knitted base fabric thread; said loop size when viewed in the circumferential direction is in the range from approx. 1-3 mm, preferably approx. 1.8 mm.

As described, the further partially interknitted threads, but also the knitted base fabric thread that is interknitted in the region of the zone and in portions is replaced by a further thread, are fixed in the knitted fabric. This preferably takes place by way of a tuck and/or float in relation to the further threads which are thus fixed in the knitted base fabric by way of a tuck and/or float. The knitted base fabric thread in this instance is inevitably fixed by way of a tuck and/or float in the loops that are knitted by way of the further threads. Fixing or "locking" that is reliable in terms of knitting technology is achieved in this way.

According to a first alternative of the invention, all part-courses can be knitted from the same thread. This means that each partially interknitted loop course which locally replaces a knitted base fabric loop course is knitted with the same thread that is thinner in comparison to the knitted base fabric thread.

Alternatively thereto, it is also conceivable that one or a plurality of part-courses is/are knitted with a first thread, and one or a plurality of part-courses is/are knitted with a second thread, wherein at least one of the two threads is thinner than the knitted base fabric thread. Two or more different further threads are thus used in the case of this design embodiment of the invention, wherein at least one of said further threads is thinner than the knitted base fabric thread while the other further thread can have, for example, a thickness that is comparable to that of the knitted base fabric thread or even a slightly greater thickness, but can differ from the properties of the knitted base fabric thread in terms of color or elasticity or the like, for example. Overall, the selection of the thickness of the further threads, even when two or more different further threads are used, is at all times be carried out such that an overall lower thread volume results in the zone than when said zone is knitted only with the knitted base fabric thread.

Both further threads are preferably thinner than the knitted base fabric thread such that each of the two threads contributes toward a reduction in the thread volume. Alternatively however, it is also conceivable that the one thread is thinner and the other thread is thicker than the knitted base fabric thread, wherein an overall reduction in the thread volume is however still provided.

According to one expedient design embodiment of the invention the part-courses when viewed in the direction of the stitch wales, can be directly mutually contiguous. When viewed in the longitudinal direction of the knitted fabric, or in the direction of the stitch wales, respectively, this means that a homogenous zone which is composed only of part-courses and which externally is comprised by the knitted base fabric is provided. The part-courses can be courses which are knitted from a same thread, or courses which are knitted from different threads, as has been described above.

Alternatively thereto it is conceivable that only every xth course is a part-course, wherein one or a plurality of knitted base fabric courses lie between two part-courses. The knitted base fabric, when viewed in the direction of the stitch wales, or in the longitudinal direction of the knitted fabric, respectively, in the case of this design embodiment of the invention is interrupted across one or a plurality of part-courses only in portions, this means that the knitted base fabric thread in the zone is interrupted in portions and in turn is encircling in other regions. For example, it is conceivable for the knitted base fabric courses and the part-courses to be mutually alternating, or for two part-courses having a knitted base fabric course lying therebetween to be knitted, for example, or a part-course having two knitted base fabric courses situated therebetween, etc.; the possibilities in terms of variations are arbitrary, wherein the part-courses here can of course also be knitted from a uniformly same thread, or from different threads, as has already been described above.

As described, the further threads, at least in part, according to the invention are thinner than the knitted base fabric thread. To the extent that the further threads are thinner than the knitted base fabric thread, said further threads should be thinner than the knitted base fabric thread by at least a factor of 0.9, particularly preferably by a factor of 0.8 (thickness of the knitted base fabric thread×factor).

The linear density of the threads or yarns used, respectively, is determined for example as in the RAL-GZ387/1 quality assurance "Medical compression hosiery" under 2.7 "Unit of linear density" in conjunction with sub-point 4.4.3 "Method for measuring the thread thickness" described measuring method. The yarn thickness of the part-courses, at least in every second course of the knitted zone, according to RAL-GZ387/1 stated above should preferably be greater than 180 dtex, to the extent that this relates to the further threads. A lower dtex number it is however also possible.

Yarn manufacturers likewise state the linear density of the yarns in the unit dtex. However, said yarn manufacturers use another measuring method. The thread weight per unit length is preferably determined according to DIN 53830 or ISO 2060. In principle, the thread weight per unit length of the further threads used, measured according to the manufacturers' specifications, should be approx. 10-30 dtex lower than the thread weight of the knitted base fabric thread, or further threads having a thickness of at least 10 dtex, preferably approx. 22 dtex should be used, respectively. The larger the difference, the easier it is for a type of knitted fabric that in the worn, thus tensioned, state is transparent in comparison to the knitted base fabric to result in the zone.

It is furthermore conceivable that the further threads at least in part have a higher elasticity than the knitted base fabric thread. When required, the compressive pressure can be maintained by using further threads of higher elasticity, this potentially being the result of a decrease in the thread volume. Any potential pressure variation that results from the reduction in volume can be counteracted by using further threads which have another elasticity than the knitted basic fabric thread, such that an overall consistent pressure profile also results within the zone and no formation of a relief zone takes place. This means that a gradual compression profile can be set or maintained, respectively, also across the zone when the knitted fabric panel is a compressive knitted fabric panel, since the elastic weft thread is encircling, thus also runs through the loop courses of the further threads, on the one hand, but influence on said compression profile can also be exerted by way of the elasticity of the further threads, on the other hand.

One refinement provides that threads which at least in part have another color than the knitted base fabric thread are used as further threads. A visual influence can be exerted in this way, and either a conscious marking of the zone across the further threads can be achieved, or a corresponding variation for reasons of design can take place.

It is furthermore possible for a plush thread which is interknitted so as to form plush loops to be provided in at least part of the part-courses or the knitted base fabric courses of the zone. A plush thread which is applied to the threads having a reduced thread linear density, thus the thinner threads, is preferably provided in the zone, said plush thread serving for configuring plush loops by way of which in turn a type of comfort zone, thus a zone that is soft in practical terms is formed. Said plush thread can be applied only to the thinner further threads; when required, said plush thread can however also be applied to the knitted base fabric thread to the extent that the latter runs through the zone. Said plush threads (optionally applied in an encircling manner as additional threads only in portions) thus enable an improvement of the wear comfort. While the thread volume is in turn indeed increased somewhat on account thereof, this increase can firstly be balanced by way of the chosen linear density of the further threads, and secondly a significant improvement in terms of comfort which is also perceptible when bending the joint results on account of said formation of a plush, as has been described.

The knitted fabric panel can be a commercially available knitted fabric panel, thus a commonplace leg stocking or the like. Alternatively, said knitted fabric panel can also be a knitted compression fabric, in particular of classes 1 to 4, as is defined in the RAL-GZ387/1 quality assurance "Medical compression hosiery", wherein said RAL document is to be applied in analogous manner to the configuration of arm stockings, for example.

The knitted fabric panel per se can be a stocking, either an arm stocking or a leg stocking, the bandage, or part of an orthosis.

Therebesides, the invention furthermore relates to a method for producing the preferably single-layer knitted fabric panel composed of a knitted base fabric knitted as a circular knitted fabric from at least one knitted base fabric thread and at least one inserted weft thread. The method is distinguished in that at least one zone having a reduced thread volume is provided, said zone being knitted by means of further threads which by way of the two ends thereof are fixed in the knitted base fabric, at least part of said further threads being thinner than the knitted base fabric thread, wherein the threads instead of the knitted base fabric thread are knitted in a plurality of separate loop-forming courses that in the circumferential direction extend by less than 360°.

At this point it is explicitly mentioned that all of the features and explanations which have been made above in terms of the knitted fabric panel apply in the same way to the method according to the invention, thus for example the description in terms of the knitting mode in relation to the sequence of the part-courses or the use of elastic or dyed threads, etc. All of the features which have been explained in the context of the knitted fabric panel according to the invention are in the same way disclosed as features of the method.

Overall, the knitted fabric panel is distinguished by, or the method according to the invention enables, respectively, the formation of a knitted fabric panel which has a specific comfort zone within the knitted base fabric, said comfort zone being reduced in terms of the thread volume. Said knitted fabric panel in the simplest case is composed of only three different threads, specifically at least one knitted base fabric thread, at least one continuous elastic weft thread, as well as one further thread, wherein alternatively two or more different knitted base fabric threads, one or a plurality of additional weft threads, or else further additional threads of different types can also be used.

Arbitrary smooth or textured yarns with or without a core can be used as threads or yarns, respectively. The threads or yarns in terms of the elasticity thereof can be comparable but can also significantly differ such that an influence on the elasticity within the zone can be exerted by way of the use of correspondingly elastic further threads so that the elasticity within the zone is determined firstly by the continuous weft thread, and secondly by the further elastic thread or threads, while the elasticity outside the zone is determined by the weft thread and the knitted base fabric thread. Setting the elasticity in the zone in comparison to the elasticity outside the zone can be achieved in a targeted manner hereby, such that a consistent homogenous pressure profile across the zone is achieved, the pressure, for example in the case of a compression stocking, consequently not changing from the knitted base fabric toward the zone and back to the knitted base fabric. Said pressure can however also be modified on account of a targeted setting of the elasticity within the zone.

In terms of knitting technology, the knitted base fabric thread and the further thread are mutually alternating in one 360° revolution in the zone. Both threads are preferably anchored or fixed, respectively, in the knitted fabric by way of a tuck and/or float. The knitted base fabric thread and the further thread only overlap in the region of only one or a plurality of neighboring stitch wales. The one thread herein is interknitted in a loop-forming manner, while the other thread is interknitted by way of a tuck and/or float; in the neighboring portion the other thread in turn is interknitted in a loop-forming manner, while the first thread is integrated by way of a tuck and/or float.

The various features of novelty which characterize the invention are pointed out with particularity in the claims annexed to and forming a part of the disclosure. For a better understanding of the invention, its operating advantages, specific objects attained by its use, reference should be had to the drawings and descriptive matter in which there are illustrated and described preferred embodiments of the invention.

DETAILED DESCRIPTION OF THE INVENTION

Figure 1:
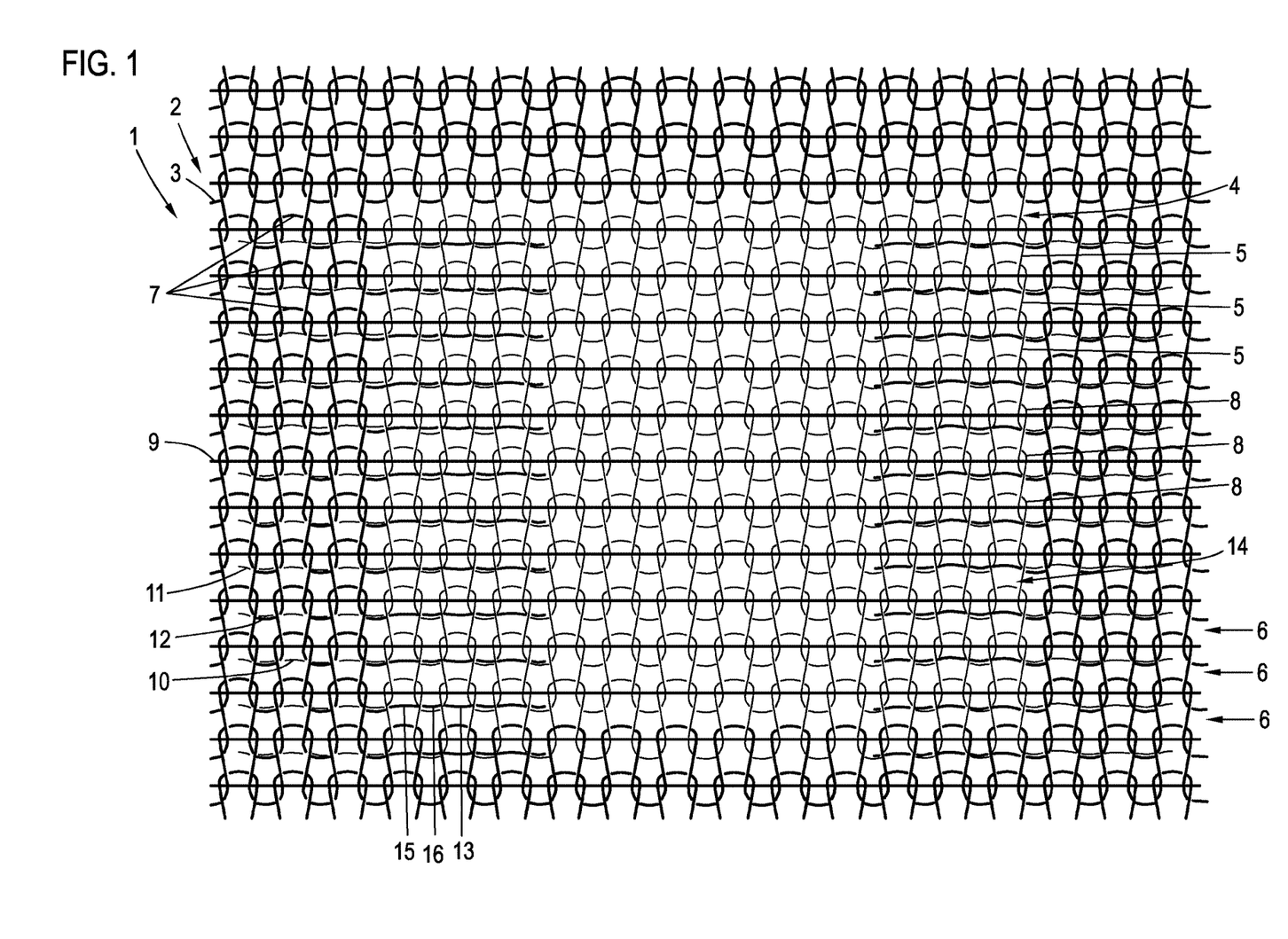
FIG. 1 shows a diagrammatic illustration of a knitted fabric panel according to the invention in a partial view, having a zone within the knitted base fabric that is knitted only from same further threads.

FIG. 1 shows a knitted fabric panel 1 according to the invention in a fragment. The knitted fabric panel 1 is, for example, a stocking, in particular a compression stocking, that means that the knitted fabric is a knitted compression fabric. The knitted fabric panel 1 is composed of a knitted base fabric 2 from at least one knitted base fabric thread 3 which here is illustrated by a thick black line.

A zone 4 in which the thread volume is reduced as compared to the thread volume in the knitted base fabric 2 is configured within the knitted base fabric 2. In the case of the exemplary embodiment according to FIG. 1, this is implemented by means of a plurality of separate further threads 5 which are interknitted in each case forming part-courses 6. While the knitted base fabric thread 3 forms the knitted base fabric loops 7 in the knitted base fabric 2, each separate further thread 5 in each part-course 6 in the zone 4 forms the loops 8 therein. As is shown by FIG. 1, the further thread 5 in each course 6 accordingly replaces the knitted base fabric thread which within the knitted base fabric 2 is encircling in a helical manner and forms the loops 7, but is interrupted in the respective loop courses in the zone 4 in the courses 6, the further thread 5 being in each case interknitted there. Consequently, this means that a defined zone 4 is formed within the knitted base fabric 2, said zone 4 being encircling by less than 360° in the circumferential direction, as the courses 6, or the further threads 5, respectively, run by less than 360°, and in the direction of the stitch wales also being delimited in terms of length.

A likewise helically encircling elastic weft thread 9 which in the example shown imparts to the knitted fabric panel 1 the substantially compressive property thereof runs through the loops 7 and 8.

In order for the thread volume within the zone 4 to be reduced in relation to the thread volume in the knitted base fabric region 2, each further thread 5 in this exemplary embodiment is thinner than the knitted base fabric thread 3, thus has a higher linear density count or a lower yarn weight, respectively. The respective further thread 5 is consequently also illustrated by means of a thinner line than the knitted base fabric thread 3.

As described, each separate thread 5 is encircling by less than 360°, thus forming only a partially interknitted course 6. Said separate thread 5 consequently has two ends 10 by way of which said further thread 5 is to be anchored in the same course in the contiguous knitted base fabric 2. As is shown by the fragment according to FIG. 1, this is implemented by way of a tuck 11 and float 12 by way of which each further thread 6 is integrated with the ends 10 in the knitted base fabric 2.

The knitted base fabric thread 3 at the transition to the zone 4 is of course inevitably also interrupted and has in each case one end 13. These two ends are also anchored by way of a tuck 15 and float 16 in the knitted fabric 14 of the zone 4, formed in each case by way of the further threads 5, and are consequently fixedly "locked" in the neighboring knitted fabric, as is each end 10.

Besides the lower thread thickness, each further thread 5 can also possess another elasticity than the knitted base fabric thread 3; said further thread 5 can be less elastic, for example, so as to optionally somewhat increase the compression in a local manner, or be more elastic so as to reduce said compression in a local manner; however, said further thread 5 can also have the same elasticity.

In any case, the interknitted zone 4 leads to an improvement in terms of comfort. The zone 4 on the knitted fabric panel 1, for example the stocking, is interknitted at a position which in the worn position comes to lie in the hollow of the knee, for example. When the knee now is bent, the knitted fabric panel 1, or the knitted loop courses, respectively, are pushed together. Since the thread volume in the zone 4 in the hollow of the knee is reduced, inevitably less "thread mass" is pushed together therein such that a decreased and less uncomfortable formation of folds arises in this region. Nevertheless, when elasticity of the further threads 5 is chosen in a corresponding manner, any potential pressure gradient remains constant, for example, or is varied by a defined degree so as to meet the requirements despite the reduced thread volume.

Figure 2:
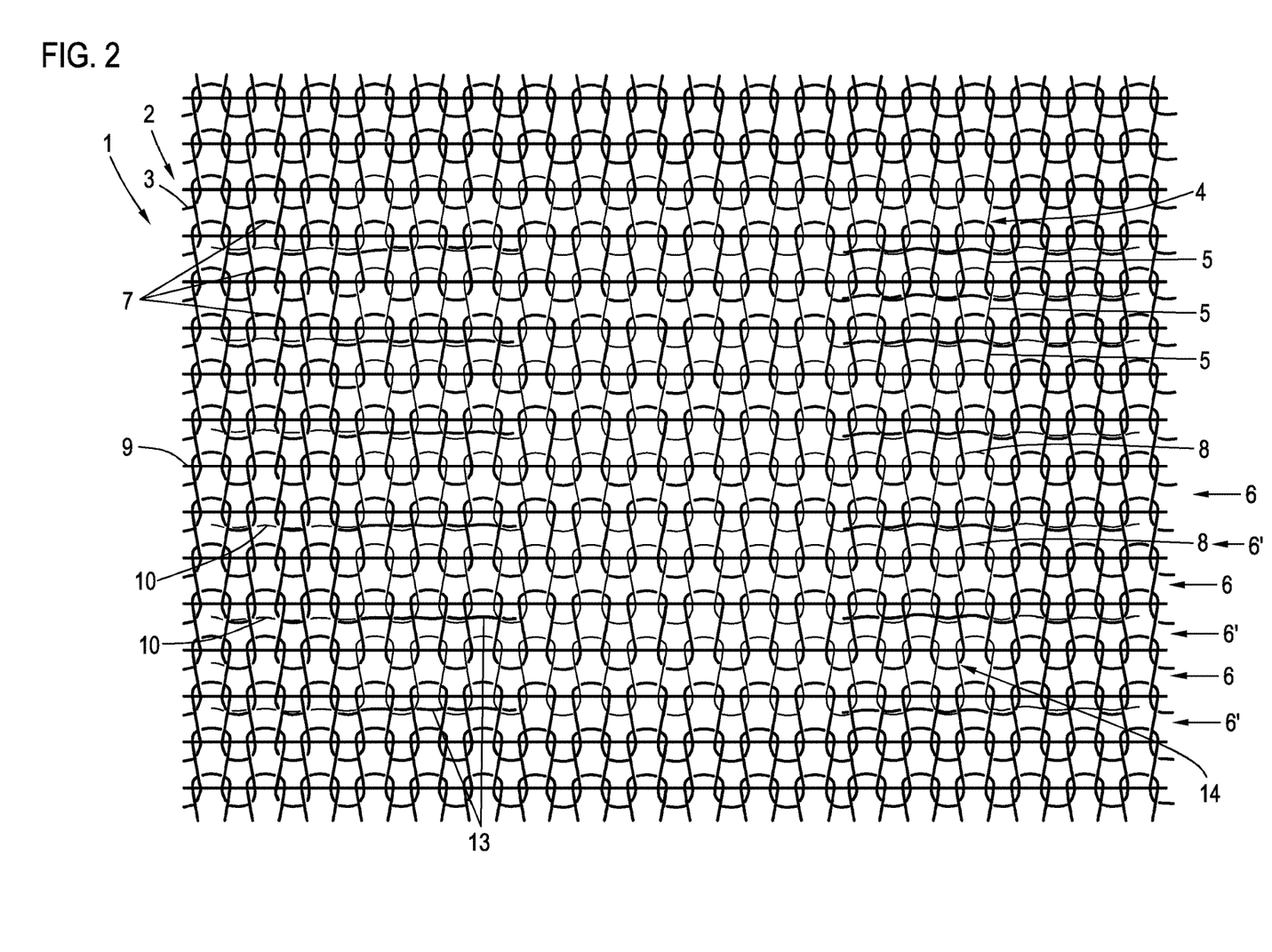
FIG. 2 shows a view corresponding to that of FIG. 1, having a zone in which knitted base fabric threads and further threads are knitted in alternating courses.

FIG. 2 shows a further exemplary embodiment of a knitted fabric panel 1 according to the invention, wherein the same reference signs are used here for the same elements. Said further exemplary embodiment is also composed of a knitted base fabric 2 composed of a knitted base fabric thread 3 which forms corresponding loops 7. A zone 4 of reduced thread volume is also provided here, said zone 4 here too being formed by way of a plurality of separate further threads 5 which are locally or partially interknitted, respectively. The further threads 5 in turn form corresponding loops 8 and here too are interknitted in local courses 6, wherein said courses 6 in the direction of the stitch wales, which run upward, are disposed so as to be in each case mutually offset by one loop course 6. One course 6' formed from the knitted base fabric thread is in each case knitted between two courses 6. This means that a reduction in the thread volume is provided in the zone 4 but to a lesser degree than in the example according to FIG. 1.

Here too, the further thread 5 is of course thinner than the knitted base fabric thread 3, thus has a significantly lower thread weight or a higher linear density count, respectively.

The anchoring of the ends 10 of the individual further threads 5 as well as of the ends 13 of the knitted base fabric thread 3 here too takes place by way of a tuck and float, in a manner similar to the exemplary embodiment according to FIG. 1.

The elastic weft thread 9 which runs helically through the knitted base fabric panel here too runs through all of the loops 7, 8 of the knitted base fabric 2 as well as of the zone 4. Alternatively, it is possible that said elastic weft thread 9 is inserted and/or interknitted so as to be at least partially loop-forming only in every nth loop course.

Figure 3:
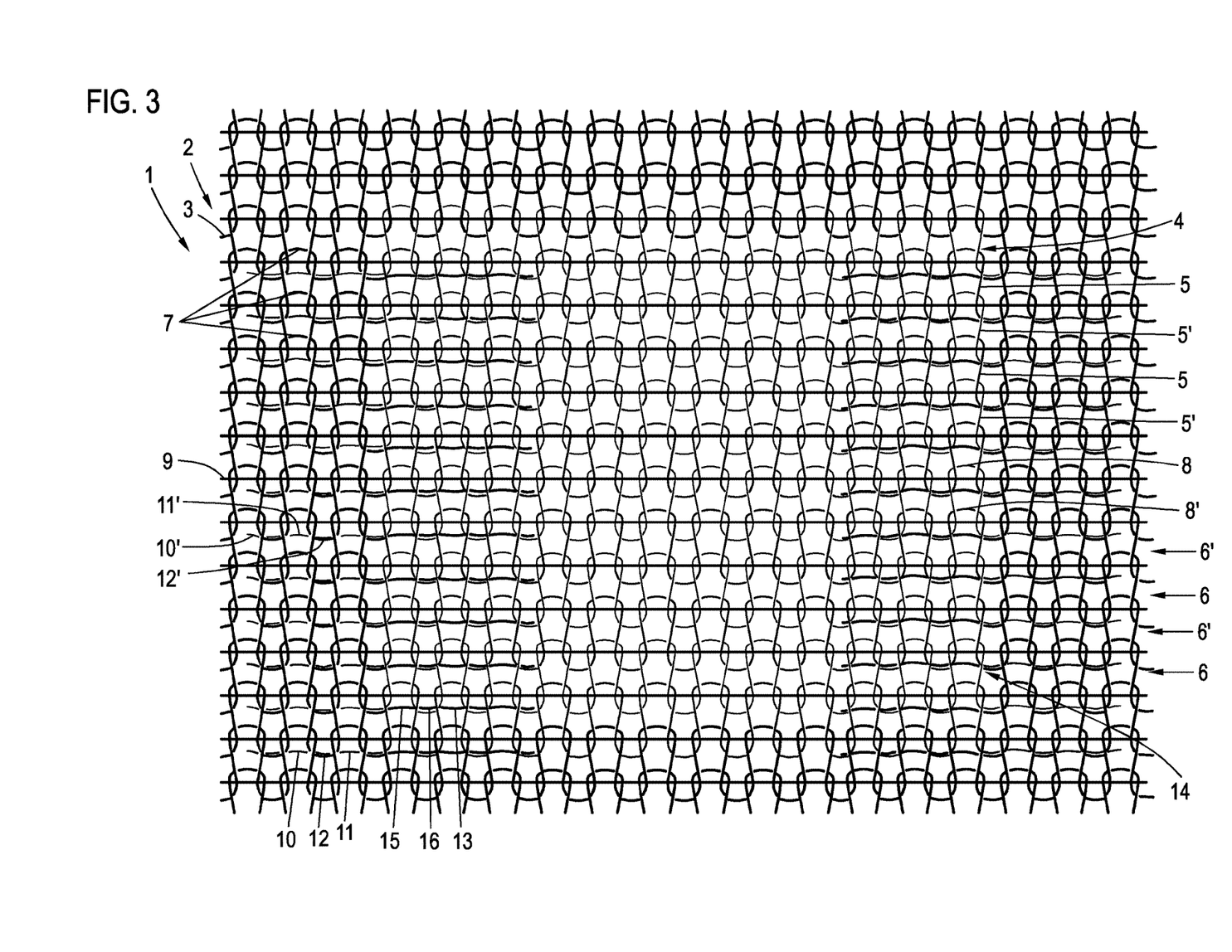
FIG. 3 shows a view corresponding to that of FIG. 1, in which two different further threads are knitted in a mutually alternating manner in the zone, wherein the one thread is thinner than the knitted base fabric thread, and the other further thread is thinner than the first further thread.

FIG. 3 shows an exemplary embodiment of a knitted fabric panel 1 comprising a knitted base fabric 2 from a knitted base fabric thread 3 which in turn forms the loops 7, and of a zone 4 which here is formed from two different further threads 5, 5'. The individual threads 5 are thinner than the knitted base fabric thread 3; the individual threads 5' are yet again thinner than the threads 5. The threads 5 in the example shown form the courses 6 which are in each case spaced apart by a loop course 6' that is formed by the thread 5'; this means that the threads 5, 5' in courses are interknitted in a mutually alternating manner.

The two ends 10 and 10' of the threads 5, 5' here too are anchored in the knitted base fabric 2 by way of a tuck 11 and float 12, or 11' and 12', respectively, while the ends 13 of the knitted base fabric thread 3 are anchored in the respective loop courses 6, 6' in a manner likewise already described by way of a tuck 15 and float 16.

A zone 4 of a significantly reduced thread volume results here too, wherein a further potential for variation in terms of the configuration of the zone, or reducing thread volume, respectively, is provided by the use of dissimilarly thin thread 5, 5'. Since the threads 5, 5' can also vary in terms of the elasticity thereof, a corresponding influence on the entire elasticity of the zone 4 and thus an influence on the elasticity of the entire knitted fabric panel 1 in this region can also be exerted.

Figure 4:
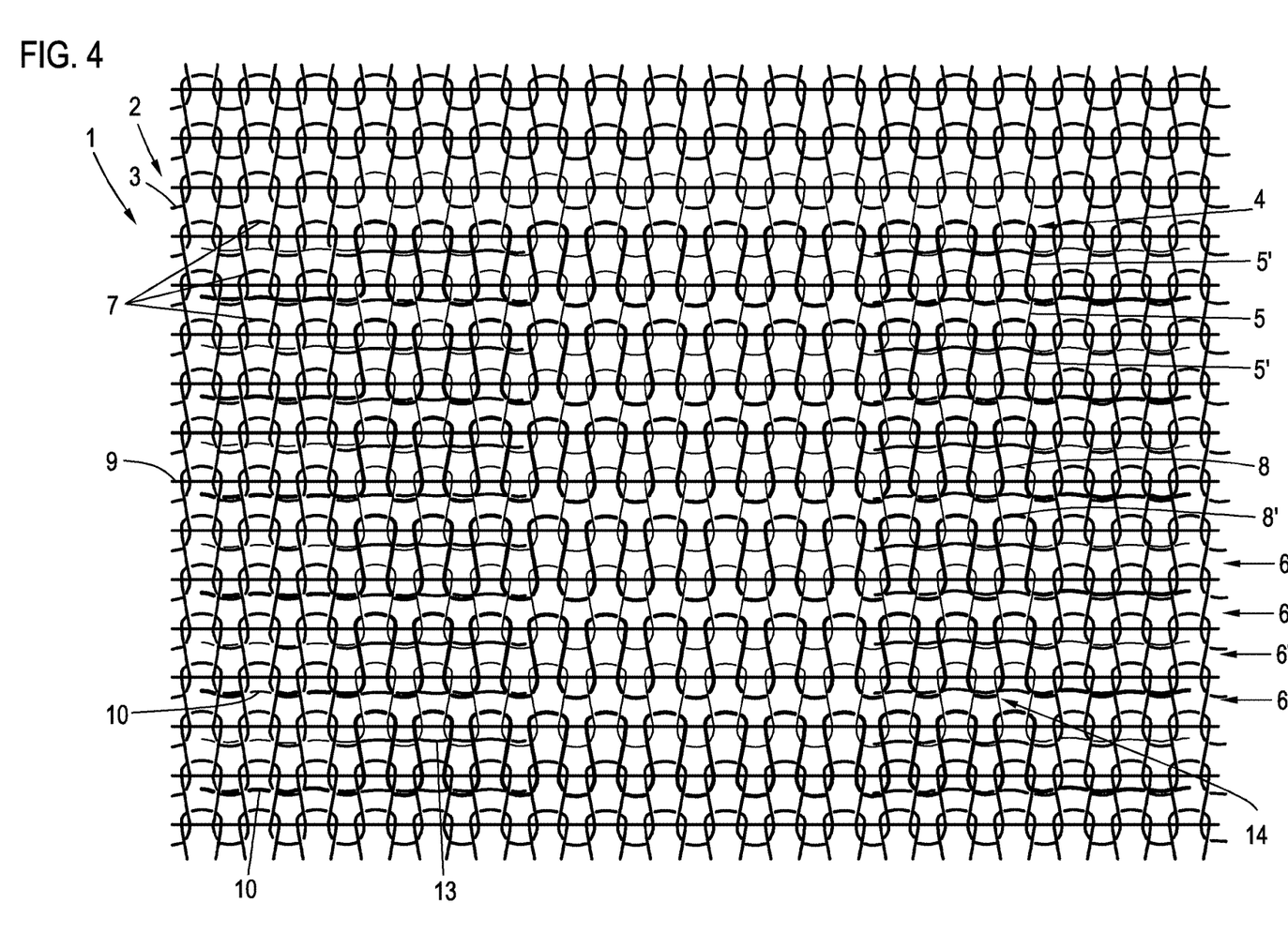
FIG. 4 shows a view corresponding to that of FIG. 1, wherein a first further thread which is thinner than the knitted base fabric thread, and a second further thread which is equally thick as or slightly thicker than the knitted base fabric thread are interknitted in the zone.

FIG. 4 shows a design embodiment of a knitted fabric panel 1 which is similar to that of FIG. 3. Here too, a knitted base fabric 2 is provided from a knitted base fabric thread 3 which is knitted so as to form loops 7, likewise a zone 4 which here too is knitted from two dissimilar threads 5, 5' which form alternating courses 6, 6'.

In the case of this design embodiment, the thread 5 is very much thinner than the knitted base fabric thread 3, while the thread 5' has a thickness that is comparable to or slightly greater than the thickness of the knitted base fabric thread 3, but in terms of the elasticity and/or coloring thereof is different in comparison to the knitted base fabric thread 3.

A reduction in the thread volume results here too, albeit not to the same degree as in the exemplary embodiments according to FIG. 1 or 2; but an exertion of influence on the entire elasticity or the coloring, etc. can be performed by way of the further thread 5' that is thicker in this case.

In a manner similar to that of FIG. 3, the elastic weft thread 9 here too runs through all of the loops 7 which are formed by the knitted base fabric thread 3, as well as the loops 8 and 8' which are formed by the threads 5, 5'.

Here too, the ends 10, 10' of the threads 5, 5' as well as the ends 13 of the knitted base fabric thread 3 are likewise anchored in the respective neighboring knitted fabric by way of a corresponding tuck and float.

Almost arbitrary threads which have a desired elasticity, thus tend to be more or less elastic, can be used as threads 3, 5, 5'. Said threads 3, 5, 5' can be embodied with or without a core; this can be smooth or textured material.

Figure 5:
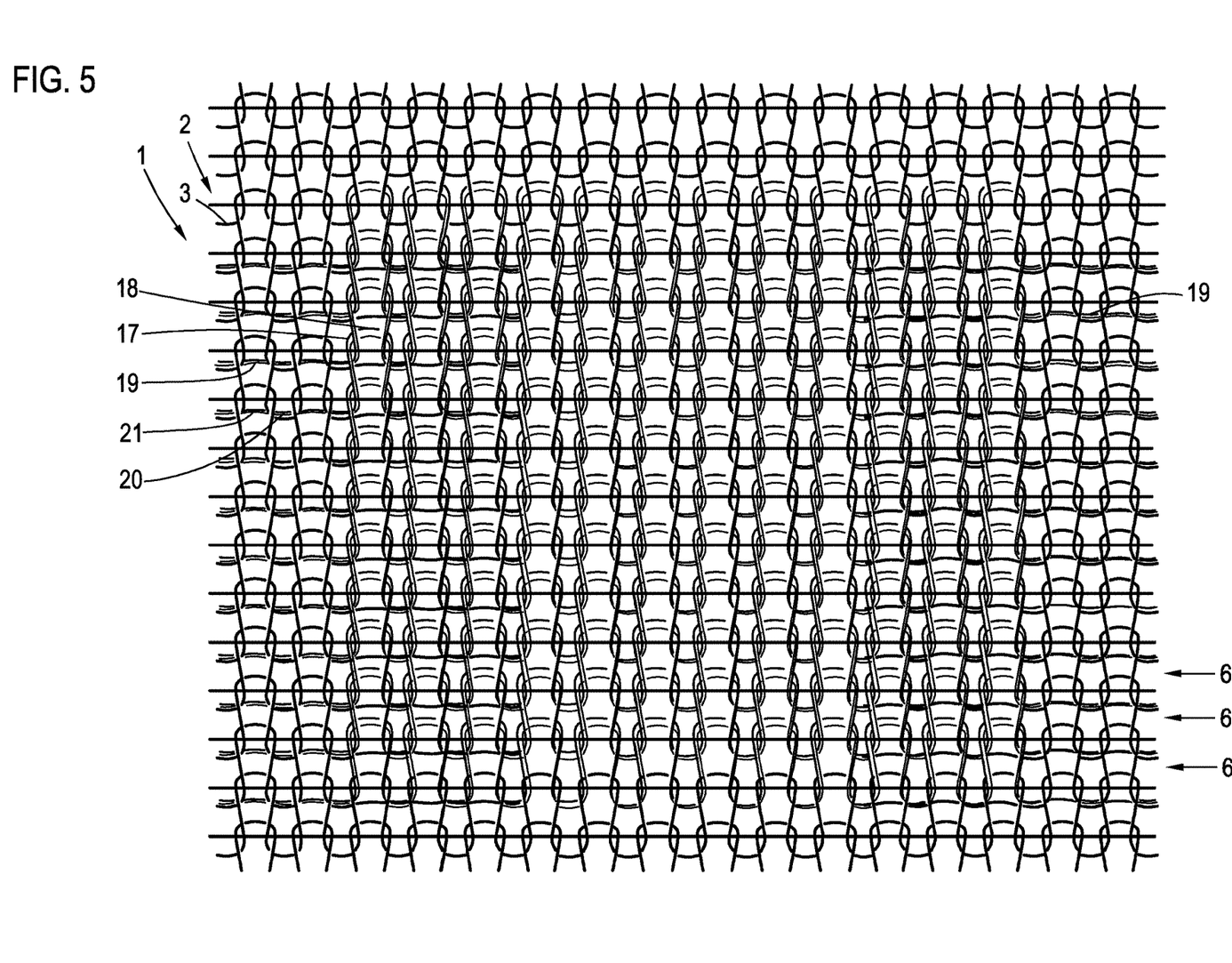
FIG. 5 shows a view corresponding to that of FIG. 1, wherein a plush thread is additionally applied here.

FIG. 5 finally shows an exemplary embodiment of a knitted fabric panel 1 which fundamentally corresponds to that from FIG. 1. Here too, a knitted base fabric 2 from a knitted base fabric thread 3 as well as an interknitted zone 4 from an additional thinner thread 5 are provided, wherein said threads 5 form in each case successive part-courses 6. The thread ends 10 are anchored in the same course in the knitted base fabric by way of a tuck and float, just as the ends 13 of the knitted base fabric thread are anchored in the knitted fabric of the zone 4 by way of a tuck and float. Reference is made to the explanations pertaining to FIG. 1.

Here however, a plush thread 17 is applied in each course 6 from the threads 5, said plush thread 17 thus being entrained and, by way of plush loops 18, bearing on the loops 8 of the threads 5. A soft comfort zone which increases the wear comfort can be formed herewith. The plush thread 17 by way of the two ends 19 thereof is likewise anchored in the same course in the knitted base fabric by means of a tuck 20 and float 21, here in a manner parallel to the thread 5 by way of the ends 10 thereof.

Such a plush thread 17 can be used in the case of all examples described, wherein said plush thread 17 can be applied to only part or all of the loops 8, 8' of the threads 5, 5', or part of the courses 6, 6', or in all courses 6, 6', respectively, or else only or additionally to potential courses 6' from the knitted base fabric thread 3 within the zone 4, wherein said plush thread 7 can of course also be applied to the knitted base fabric thread 3 outside the zone 4. The thread is particularly preferably applied to the knitted base fabric thread and/or further threads in such a manner that said thread configures a so-called sandwich plush.

It is crucial herein that a thread volume that is reduced in comparison to the neighboring knitted base fabric zone is provided in the zone 4. The transition from the zone 4 to the region of the knitted base fabric 3 is fluid and accurate to a needle, as one loop 7 of the knitted base fabric 2 adjoins in each case one loop 8 or 8' of the zone 4 in the two neighboring stitch wales, and the respective thread end 10, 10', or 13, respectively, runs out by way of a tuck and float in the respective neighboring knitted fabric region.

The thinner the further threads 5, 5' in the zone 4, the more transparent the knitted fabric 14 in said zone 4 can be knitted in comparison to the knitted base fabric 2, this optionally being advantageous for the visual appeal since a transparent or semi-transparent knitted fabric 14 can be configured.

If the knitted fabric 1 is a knitted compression fabric, an almost consistent pressure gradient can be achieved in the circumferential direction as well as in the direction of the stitch wales, despite the integration of the zone 4 which serves the purpose of comfort, in that a corresponding choice of the elasticity of the further threads 8, 8' can be achieved despite the significantly reduced thickness of said further threads 8, 8'. This means that less thread material is situated in the region of the bend of the joint, at an almost identical compression.

The loop size in the zone 4 can also be almost identical to the loop size in the knitted base fabric 2; this means that no difference in purely visual terms between the zones results when desired, to the extent that said difference is not consciously accepted, for example by using extremely thin further threads 8, 8' or by using correspondingly dyed threads 8, 8', etc.

While specific embodiments of the invention have been shown and described in detail to illustrate the inventive principles, it will be understood that the invention may be embodied otherwise without departing from such principles.

I claim:

1. A knitted fabric panel, composed of a knitted base fabric knitted as a circular knitted fabric from at least one knitted base fabric thread, wherein at least one zone having a reduced thread thickness is provided, said zone being knitted by additional threads which by way of the two ends thereof are fixed in the knitted base fabric, at least part of said additional threads being thinner than the knitted base fabric thread, wherein the additional threads, instead of the knitted base fabric thread, are knitted in a plurality of separate loop forming courses that extend by less than 360° in a circumferential direction.

2. The knitted fabric panel according to claim 1, wherein the additional threads are fixed in the knitted base fabric by a tuck.

3. The knitted fabric panel according to claim 1, wherein one or a plurality of separate courses is/are knitted with a first thread, and one or a plurality of separate courses is/are knitted with a second thread, wherein at least one of the two threads is thinner than the knitted base fabric thread.

4. The knitted fabric panel according to claim 3, wherein both the first and the second threads are thinner than the knitted base fabric thread.

5. The knitted fabric panel according to claim 3, wherein the first thread is thinner and the second thread is thicker than the knitted base fabric thread.

6. The knitted fabric panel according to claim 1, wherein the separate courses when viewed in the direction of the stitch wales, are directly mutually contiguous.

7. The knitted fabric panel according to claim 1, wherein that only every $x^{th}$ course is a separate course, wherein one or a plurality of knitted base fabric courses lie between two separate courses.

8. The knitted fabric panel according to claim 1, wherein the additional threads, to the extent that said further threads are thinner than the knitted base fabric thread, are thinner than the knitted base fabric thread by at least a factor of 0.9.

9. The knitted fabric panel according to claim 1, wherein the additional threads at least in part have different elasticity than the knitted base fabric thread.

10. The knitted fabric panel according to claim 1, wherein the additional threads at least in part have another color than the knitted base fabric thread.

11. The knitted fabric panel according to claim 1, wherein a plush thread which is interknitted so as to form plush loops is provided in at least part of the separate courses or the knitted base fabric courses of the zone.

12. The knitted fabric panel according to claim 1, wherein said knitted fabric panel is a knitted compression fabric.

13. The knitted fabric panel according to claim 12, wherein at least one weft thread is inserted in the knitted base fabric.

14. The knitted fabric panel according to claim 1, wherein said knitted fabric panel is a stocking, a bandage, or part of an orthosis.

15. A method for producing a knitted fabric panel composed of a knitted base fabric knitted as a circular knitted fabric from at least one knitted base fabric thread and at least one inserted weft thread, wherein at least one zone having a reduced thread thickness is provided, said zone being knitted by additional threads which by way of the two ends thereof are fixed in the knitted base fabric, at least part of said additional threads being thinner than the knitted base fabric thread, wherein the additional threads, instead of the knitted base fabric thread, are knitted in a plurality of separate loop forming courses that extend by less than 360° in a circumferential direction.

16. The knitted fabric panel according to claim 1, wherein the additional threads are fixed in the knitted base fabric by a float.

17. The knitted fabric panel according to claim 2, wherein the additional threads are fixed in the knitted base fabric by a tuck and a float.

18. The knitted fabric panel according to claim 8, wherein the additional threads are thinner than the knitted base fabric thread by at least a factor of 0.8.

19. The knitted fabric panel according to claim 12, wherein at least one weft thread is interknit in the knitted base fabric.

20. The knitted fabric panel according to claim 13, wherein at least one weft thread is inserted and interknit in the knitted base fabric.

\* \* \* \* \*